United States Patent [19]

Torii et al.

[11] 4,336,202
[45] Jun. 22, 1982

[54] 1,3-CYCLOHEXANEDIONE DERIVATIVES

[75] Inventors: Sigeru Torii; Kenji Uneyama, both of Okayama; Takashi Onishi, Kurashiki; Yoshiji Fujita, Kurashiki; Michihiro Ishiguro, Kurashiki; Takashi Nishida, Kurashiki, all of Japan

[73] Assignee: Kuraray Co., Ltd., Kurashiki, Japan

[21] Appl. No.: 264,463

[22] Filed: May 18, 1981

[30] Foreign Application Priority Data

May 29, 1980 [JP] Japan .................................. 55-72406
Jun. 12, 1980 [JP] Japan .................................. 55-79702

[51] Int. Cl.³ .................. C07D 307/83; C07C 49/403
[52] U.S. Cl. .................................. 549/466; 204/59 R; 568/376; 548/516
[58] Field of Search ..................... 260/346.22; 568/376

[56] References Cited

U.S. PATENT DOCUMENTS 4,119,646 10/1978 Heiba et al. ................. 260/346.22

Primary Examiner—John M. Ford
Assistant Examiner—Bernard Dentz
Attorney, Agent, or Firm—Burns, Doane, Swecker & Mathis

[57] ABSTRACT

Novel cyclohexanone derivatives of general formula:

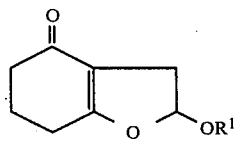

(wherein $R^1$ is a hydrocarbon group of 1 to 15 carbon atoms) and new cyclohexanone derivatives of general formula:

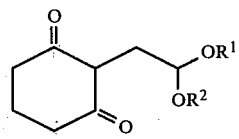

(wherein $R^1$ and $R^2$ each is a hydrocarbon group of 1 to 15 carbon atoms) are produced by an electrooxidative coupling of 1,3-cyclohexanedione with a vinyl ether of general formula:

$$CH_2=CH-O-R^1$$

(wherein $R^1$ is as defined above) in the presence or absence of an alcohol of general formula:

$$R^2OH$$

(wherein $R^2$ is as defined above). These new cyclohexanone derivatives can be easily converted to N-substituted or unsubstituted-4-oxo-4,5,6,7-tetrahydroindoles, which are of value as intermediates for the production of N-substituted or unsubstituted-4-hydroxyindoles and, thence, to pindolol and its analogs.

5 Claims, No Drawings

1,3-CYCLOHEXANEDIONE DERIVATIVES

BACKGROUND OF THE INVENTION

1. Field of the Invention

This invention relates to novel cyclohexanone derivatives, a method of producing the same derivatives by an electrooxidative coupling of 1,3-cyclohexanedione with a vinyl ether in the presence or absence of an alcohol, and a method of producing 4-oxo-4,5,6,7-tetrahydroindoles from said cyclohexanone derivatives.

2. Description of the Prior Art

It is known that 4-oxo-4,5,6,7-tetrahydroindole can be transformed via its dehydrogenation product 4-hydroxyindole into pindolol, which is well-known adrenergic β-blocking agent, or its related compounds.

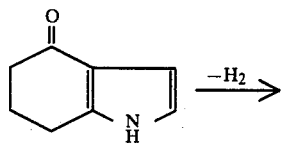

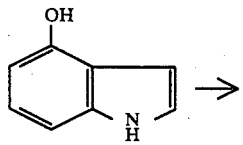

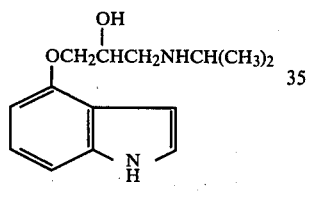

Pindolol

Heretofore, the following processes have been proposed for the synthesis of 4-oxo-4,5,6,7-tetrahydroindole from 1,3-cyclohexanedione as the starting material.

(A) The process in which 1,3-cyclohexanedione is reacted with oxyiminoglyoxal in the presence of acetic acid and zinc metal (Japanese Patent publication No. 9904/1969). This reaction may be written as follows.

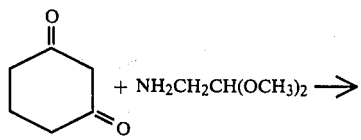

(B) The process in which 1,3-cyclohexanedione is reacted with aminoacetaldehyde dimethyl acetal in the presence of p-toluenesulfonic acid [J. Chem. Soc. Commun., 1429 (1968), J. Org. Chem. 43, 3541 (1978)]. This reaction may be written as follows.

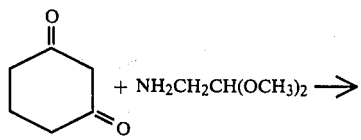

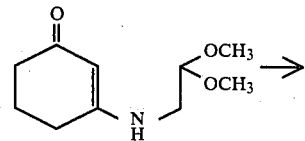

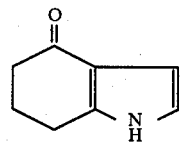

(C) The process in which 1,3-cyclohexanedione is reacted with an alkyl halopyruvate and the resultant 4-oxo-4,5,6,7-tetrahydrocoumarone-3-carboxylic acid is further reacted with ammonia [Japanese Patent Application Kokai (laid open) No. 19971/1979].

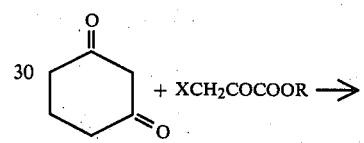

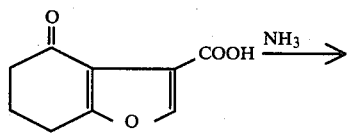

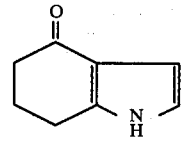

[wherein X is a halogen atom; R is an alkyl group].

The above processes (A) and (B) are disadvantageous in that no satisfactory yield or selectivity can be obtained, although the reaction procedures are rather easy to follow. The process (C) provides for a relatively high yield in each of the reaction steps but since one of the reactants, i.e. alkyl halopyruvate, is not readily available from commercial sources, the process for preparing this reactant is additionally required. Therefore, despite the fact that the starting compound 1,3-cyclohexanedione is commercially available readily and at a comparatively low cost, the conventional processes have disadvantages in regard to the yield or selectivity of reaction or the availability of the starting material other than 1,3-cyclohexanedione.

SUMMARY OF THE INVENTION

It has now surprisingly been found that the above-mentioned disadvantages are readily obviated by providing novel compounds having the following general formula (I) or (II):

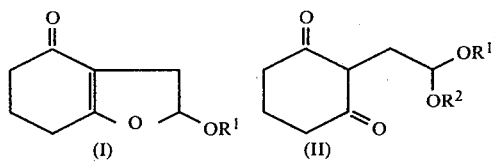

[In bth formulas (1) and (2), $R^1$ and $R^2$ each represents a hydrocarbon group of 1 to 15 carbon atoms.]

It has been found that compounds of formula (I) and those of formula (II) can be produced easily and in good yield in a single step from 1,3-cyclohexanedione and a vinyl ether which is readily available, or from both starting compounds plus an alcohol. It has been further found that compounds of formula (I) and compounds of formula (II) may react readily with ammonia, an ammonium salt, a primary amine or a salt thereof to give 4-oxo-4,5,6,7-tetrahydroindole or an N-substituted product thereof in high yield. It was also found that the electrochemical reaction mixture containing the product compound (I) or (II) may as such be directly used in the subsequent reaction with ammonia, ammonium salt, primary amine or salt thereof and that, even then, said subsequent reaction may be satisfactorily conducted substantially without inducing undesirable side reactions.

Therefore, compounds (I) and (II) of the present invention are very useful as intermediates for the production of 4-hydroxyindole or N-substituted-4-hydroxyindoles and, hence, of pindolol and its analogs.

DETAILED DESCRIPTION OF THE INVENTION

More particularly, in accordance with this invention, 1,3-cyclohexanedione and a vinyl ether of general formula (III):

$$CH_2=CH-O-R^1 \qquad (III)$$

[wherein $R^1$ is as defined for formula (I)] are subjected to an electrochemical (electrooxidative coupling) reaction, in the presence or absence of an alcohol of general formula (IV):

$$R^2OH \qquad (IV)$$

[wherein $R^2$ is as defined for formula (II)], under basic conditions to thereby produce a compound of formula (I) in the absence of said alcohol or a compound of formula (I) and a compound of formula (II) in the presence of said alcohol, in high selectivity and high yield. This is surprising in view of the fact that when 1,3-cyclohexanedione is reacted with a vinyl ether by any of the conventional methods other than the electrochemical method, the diacetal compound is predominantly produced in the following series of reaction.

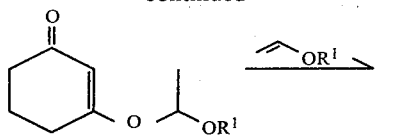

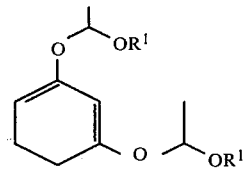

The reaction mechanism involved in the electrochemical method of this invention has not been fully elucidated, but a tentative reaction mechanism is shown in the following scheme.

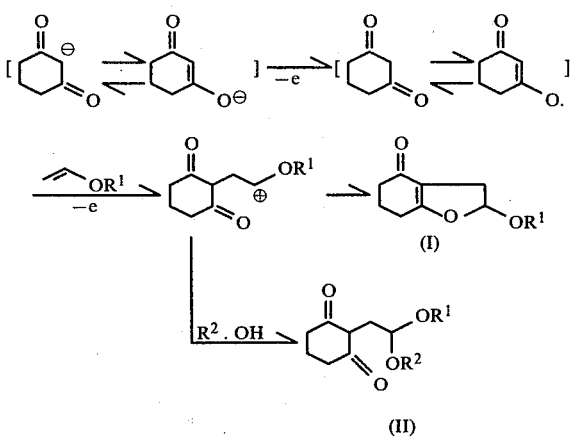

Fundamentally, the electrochemical or electrooxidative coupling reaction according to this invention is carried out by passing an electric current through a mixture of 1,3-cyclohexanedione and a vinyl ether in the presence of a basic compound which renders the reaction system basic. The basic compound is preferably a compound which is inert to the starting compounds, reaction product and solvent used and which would not interfere with the electrooxidative reaction. Among such preferred basic compounds are the oxides, hydroxides, carbonates, acetates and alkoxides (e.g. methoxides, ethoxides, propoxides, butoxides) of alkali metals or alkaline earth metals such as lithium, sodium, potassium, calcium, barium, etc. and tertiary amines (such as tri-lower alkylamines, e.g. trimethylamine, triethylamine, etc.; cyclic amines, e.g. pyridine, picoline, pyrimidine, ricidine, quinoline, etc; and so on. Particularly desirable basic compounds are the alkoxides and hydroxides of alkali metals or alkaline earth metals, and tertiary amines and mixtures thereof. While the basic compound is used in a sufficient amount to maintain a basic reaction system, a proportion of 0.1 to 10 molar equivalents based on 1,3-cyclohexanedione is desirable in view of selectivity of the reaction.

Referring to the general formula (III) of the vinyl ether to be reacted with 1,3-cyclohexanedione, $R^1$ is a hydrocarbon group containing, mainly for economic reasons, not more than 15 carbon atoms. Thus, there may be mentioned, for example, alkyl groups of 1 to 15 carbon atoms (e.g. methyl, ethyl, n-propyl, isopropyl, n-butyl, isobutyl, tert-butyl, n-pentyl, isopentyl, n-hexyl, n-octyl, cyclohexylmethyl, etc.), cycloalkyl groups of 3 to 15 carbon atoms (e.g. cyclopropyl, cyclopentyl, cyclohexyl, methylcyclohexyl, etc.), aryl groups of 6 to 15 carbon atoms (e.g. phenyl, tolyl, xylyl, etc.), and aralkyl groups of 7 to 15 carbon atoms (e.g. benzyl, phenylethyl, p-methylbenzyl, etc.). For practical purposes, the number of carbon atoms in the hydrocarbon group is desirably up to 10. Usually, the vinyl ether is preferably used in an excess amount with respect to 1,3-cyclohexanedione. While a large excess may be employed, it is generally unnecessary to use more than 30 molar equivalents of the vinyl ether. In consideration of the reaction result and the recovery of unreacted material, it is desirable to use the vinyl ether in an amount ranging from 2 to 25 moles per mole of 1,3-cyclohexanedione.

For the improvement of reaction rate and selectivity, the electrochemical reaction is preferably conducted in the presence of a solvent. There is no particular limitation on the type of solvent, only if it is capable of providing a homogeneous reaction system and will not interefere with, or will rather promote, the contemplated electrochemical reaction. Examples of usable solvents are methanol, ethanol, propanol, butanol, ethylene glycol, propylene glycol, 1,4-butanediol, 3-methyl-1,3-butanediol, dimethylformamide, diethylformamide, dimethylacetamide, diethylacetamide, acetonitrile, propionitrile, dimethyl carbonate, diethyl carbonate, nitromethane, dimethyl sulfoxide, methylene chloride, methyl acetate, ethyl acetate, etc., as well as mixtures of such solvents. When a tertiary amine is employed as said basic compound, it may function as the solvent as well. Moreover, provided that the reaction mixture may be maintained in a substantially homogeneous condition, water may be employed in combination with an organic solvent such as those mentioned above. Particularly, an alcoholic solvent is conducive to increased reaction rate and selectivity. Alcohols which are readily available and easy to use are those having the general formula (IV) given hereinbefore. In the formula (IV), the $C_{1-15}$ hydrocarbon group $R^2$ is preferably a $C_{1-15}$ alkyl group, a $C_{5-15}$ cycloalkyl group, or a $C_{7-15}$ aralkyl group. Preferred examples of alcohol (IV) include, in addition to the lower alkanols previously mentioned, such comparatively higher alcohols as isoamyl alcohol, octyl alcohol, capric alcohol, nonyl alcohol, lauryl alcohol, myristyl alcohol, cyclopentanol, cyclohexanol, methylcyclohexanol, isopropylcyclohexanol, benzyl alcohol, methylbenzyl alcohol, phenylethyl alcohol, etc. The alkanols having up to 10 carbon atoms and cycloalkanols having up to 10 carbon atoms are practically useful. These alcohols are desirably used alone or as a mixture, or together with a small proportion of other solvents. Even if the alcohol is solid at the reaction temperature, it is serviceable when used in combinatin with another solvent which solubilizes the alcohol. While the amount of the solvent is not critical, it is practically advantageous to use 0.1 to 100 l, preferably 0.5 to 20 l, of the solvent for each mole of 1,3-cyclohexanedione.

While the alcohol is a suitable reaction solvent, it is reactive to the carbonium ion as is apparent from the reaction formulas given hereinbefore and, accordingly, gives rise to compound (II) as well. Thus, when the reaction is conducted in the presence of alcohol (IV), there is generally produced a mixture of compounds (I) and (II). Since compounds (II) and (I) can be converted to 4-oxo-4,5,6,7-tetrahydroindoles under the identical reaction conditions, the two compounds (I) and (II) are equivalent within the purview of this invention and it is not a disadvantage that the (I) and (II) are simultaneously produced in the electrochemical reaction according to this invention. Therefore, the yield according to this invention is expressed as, or based on, the sum of the yields of (I) and (II). While the alcoholic solvent may be an alcohol as such or a mixed solvent containing at least one volume percent of alcohol, the amount of alcohol in such a mixed solvent is preferably at least equimolar to 1,3-cyclohexanedione. When the reaction is conducted in the presence of such a solvent, the compound (I) is usually produced in an approximately equimolar to predominant proportion relative to compound (II). While compounds (I) and (II) can be separated from each other by a known procedure such as distillation in high vacuum or chromatography, such a separation procedure is unnecessary when the compounds are intended to be intermediates for the production of 4-oxo-4,5,6,7-tetrahydroindoles.

The basic compound used in the electrochemical reaction generally acts as a supporting electrolyte and, therefore, it is usually unnecessary to employ any other supporting electrolyte. When, however, the concentration of the basic compound is too low to ensure a desired current density or the basic compound is not a supporting electrolyte, it is necessary to incorporate in the reaction system an auxiliary supporting electrolyte such as an ammonium salt or a salt of an alkali or alkaline earth metal (e.g., lithium, sodium, potassium, barium, calcium, strontium, magnesium, etc.), for example, chloride, sulfate, phosphate, perchlorate, tosylate or the like. The type and amount of such an auxiliary supporting electrolyte are selected so that the basicity of the reaction system will be sustained, and generally its amount is about 0.1% to saturation, particularly about 0.5% to 1% by weight, based on the weight of 1,3-cyclohexanedione.

The electrode can be selected from among those commonly used in general electrochemical processes, such as gold, platinum, gold- or platinum-plated titanium or nickel, carbon, titanium, nickel, stainless steel, lead, copper and so on. The electrode metals which are satisfactory in terms of reaction yield and selectivity are platinum, nickel, stainless steel, carbon and lead. The current density may range from 5 to 500 $mA/cm^2$ and preferably from 10 to 200 $mA/cm^2$. From the standpoints of current efficiency and reaction selectivity, the range of 10 to 50 $mA/cm^2$ is particularly desirable. This value can be controlled by varying the applied voltage.

According to the reaction formula shown hereinbefore for the reaction mechanism, the required quantity of electricity is 2 faradays per mole of 1,3-cyclohexanedione but actually it is preferable to increase the selectivity of the reaction to compound (I) and/or compound (II) by using 1 to 2 faradays/mole. While the reaction can be conducted at a temperature within a comparatively broad range from $-20°$ C. to $+80°$ C., it is practically advantageous to conduct the reaction at $0°$ to $50°$ C., and especially at ambient temperature. The electrochemical oxidation reaction according to this invention is an exothermic reaction, and the reaction initiated at room temperature, for instance, may cause the system temperature to build up to about $40°$ C. While the reaction is not critically temperature-dependent, the reaction system may be cooled or heated by a conventional procedure, if a constant reaction temperature is considered to be desirable. The electrochemical reaction system may contain other components that will not interfere with the reaction.

In the practice of this invention, the electrochemical oxidation reaction may be conducted either in a continuous manner or batch-wise. Recovery of the product from the reaction mixture can be carried out by the conventional procedure such as extraction with a suitable solvent but for the production of 4-oxo-4,5,6,7,-tetrahydroindoles, the reaction mixture as it is can be directly submitted to the reaction.

The group $R^1$ in the compound (I), which is one of the products in accordance with the invention, is as mentioned with regard to the group $R^1$ in the vinyl ether of formula (III). The groups $R^1$ and $R^2$ in the compound (II), another product in accordance with the invention, are as mentioned with regard to the group $R^1$ in the vinyl ether of formula (III) and the group $R^2$ in the alcohol of formula (IV), respectively. In view of the fact that the groups $OR^1$ and $OR^2$ in the compounds (I) and (II) are eliminated in the course of production of 4-oxo-4,5,6,7-tetrahydroindoles from these compounds, the group $R^1$ is desirably such that the vinyl ether of formula (III) has a good reactivity toward 1,3-cyclohexanedione, and the group $R^2$ to be such that the alcohol of formula (IV) brings about a high rate of reaction with a high selectivity. It is also desirable that the groups $R^1$ and $R^2$ are each of an economically advantageous origin. From the above point of view, $R^1$ is desirably a lower alkyl group (e.g. ethyl, propyl, n-butyl, i-butyl), a phenyl group or a benzyl group, and $R^2$ is desirably a lower alkyl group (e.g. methyl, ethyl, propyl, n-butyl, i-butyl), or a cyclohexyl group.

In the context of this invention, compounds (I) and (II) encompass any and all stereoisomers that may exist and are not limited to any particular member thereof.

Reaction of a compound (I) and/or compound (II) with ammonia, an ammonium salt or a primary amine of general formula (V):

[$R^3$ is a hydrocarbon group of 1 to 10 carbon atoms] or a salt thereof (hereinafter, these nitrogen-containing compounds are sometimes referred to collectively as an aminating agent) gives an 4-oxo-4,5,6,7-tetrahydroindole or N-substituted-4-oxo-4,5,6,7-tetrahydroindole of general formula (VI):

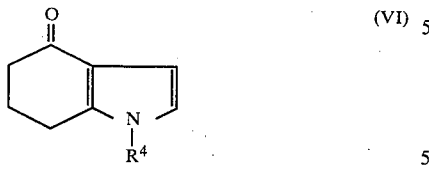

[wherein $R^4$ is a hydrogen atom or the same hydrocarbon group as $R^3$ of formula (V)] in high yield.

This reaction can be carried out by a method analogous to the conventional method known per se for substitution of a nitrogen atom for the oxygen atom of an oxygen-containing heterocyclic compound [e.g., the transformation of furan ring-containing compounds into pyrrole derivatives as described in Ann. 655, 20 (1962)]. This reaction can usually be conducted by mere heating of compound (I) and/or compound (II) with said aminating agent. The heating temperature may be selected with reference to the desired reaction rate and economic factors, and ranges usually from 50° to 200° C. and preferably from 70° to 150° C.

No consideration need be given to the reaction pressure except that it may be needed to carry out the reaction under elevated pressure for prevention of evaporation of the reactant, solvent and other components contained in the reaction system under the selected reaction conditions.

The practically desirable amount of the aminating agent is about 1 to 5 moles per mole of the compounds (I) and (II) combined. While the aminating agent may be employed in a large excess, it is meaningless to employ, for example, more than 20 moles, especially more than 50 moles of the aminating agent per mole of the compounds (I) and (II) combined.

While the reaction solvent is not essential, an aprotoic nonpolar or polar solvent that will not interfere with the reaction can be employed so as to facilitate control of the reaction.

Prior to reaction with the aminating agent, compound (I) and/or compound (II) can be hydrolyzed with an acid such as mineral acids (e.g. dilute HCl, dilute $H_2SO_4$, boric acid), Lewis acids (e.g. zinc chloride, zinc bromide, ferric chloride), etc. to give compounds wherein $R^1$ and/or $R^2$ is a hydrogen atom. This procedure, however, is not essential from the standpoints of yields of 4-oxo-4,5,6,7-tetrahydroindoles and selectivity of the reaction to these compounds.

The surrounding gas of the reaction system may be air or an inert gas such as nitrogen, argon, helium or the like.

Referring to the aminating agent, the ammonium salts of organic acids are generally the ammonium salts of monocarboxylic acids such as formic acid, acetic acid, propionic acid, butyric acid, valeric acid, pivalic acid, lauric acid, myristic acid, palmitic acid, stearic acid, benzoic acid, dimethylbenzoic acid, polycarboxylic acids such as oxalic acid, malonic acid, succinic acid, glutaric acid, adipic acid, sebacic acid, phthalic acid, etc. and sulfonic acids such as benzenesulfonic acid, toluenesulfonic acid, etc. Examples of ammonium salts of inorganic acids include the ammonium salt of hydrogen halides such as ammonium chloride, ammonium bromide, etc., ammonium sulfate, ammonium phosphate, ammonium carbonate, ammonium borate, etc. When such ammonium salt of organic or inorganic acid is employed as the aminating agent, the reaction product compound is the compound of formula (VI) wherein $R^4$ is a hydrogen atom, i.e. 4-oxo-4,5,6,7-tetrahydroindole. When, in accordance with this invention, an amine of formula (V) or a salt thereof is used as said aminating agent, the reaction product compound is the compound of formula (VI) wherein $R^4$ is the same as $R^3$ of formula (V), i.e. 1-hydrocarbyl-4-oxo-4,5,6,7-tetrahydroindole. The number of carbon atoms in the hydrocarbon group $R^3$ of formula (V) is usually limited to a value of 1 to 10 but if the number of carbon atoms in $R^3$ exceeds 10, the reaction as such is not materially influenced. The said hydrocarbon group may be a saturated or unsaturated group and may be either acyclic or cyclic. For example, there may be mentioned $C_{1-10}$ alkyl groups (e.g. methyl, ethyl, n-propyl, isobutyl, tert-butyl, n-pentyl, 3-methylbutan-1-yl, n-hexyl, cyclohexylmethyl, cyclopentylmethyl, octyl, etc.), $C_{3-10}$ alkenyl groups (e.g. allyl, 3-buten-1-yl, 3-methyl-3-buten-1-yl, 3-methyl-2-buten-1-yl, 4-penten-1-yl, 4-methyl-3-penten-1-yl, citroneryl, 1,3-butadienyl, geranyl, etc.), $C_{3-10}$ cycloalkyl groups (e.g. cyclopropyl, cyclopentyl, cyclohexyl, methylcyclohexyl, etc.), $C_{5-10}$ cycloalkenyl groups (e.g. cyclopentenyl, cyclohexenyl, methylcyclohexenyl, etc.), $C_{6-10}$ aryl groups (e.g. phenyl, tolyl, xylyl, naphthyl), and $C_{7-10}$ aralkyl groups (e.g. benzyl, phenylethyl, methylbenzyl, etc.). The salt of amine (V) includes the salts of organic acids and inorganic acids mentioned in connection with the ammonium.

Some representative species of compounds (VI) are as follows.

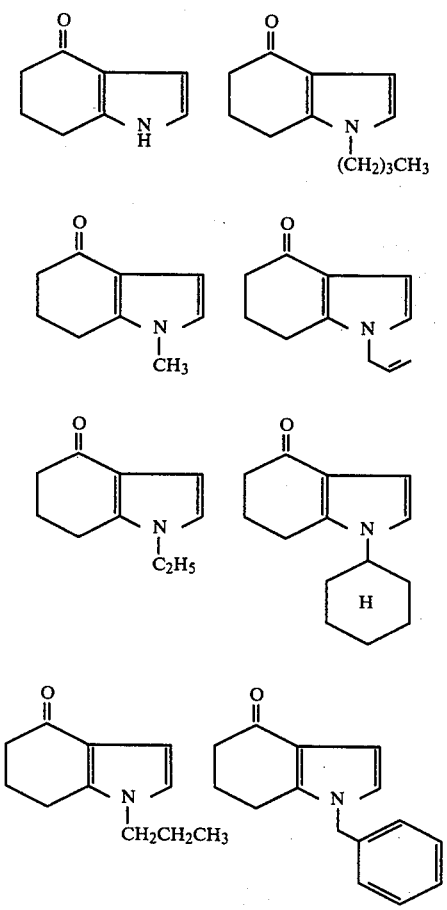

The 4-oxotetrahydroindoles (VI) can be converted to 4-hydroxyindoles by dehydrogenation reaction which is known per se [e.g. Chem. Ber. 101, 2605 (1968), J. Heterocycle Chem., 14, 71 (1977)]

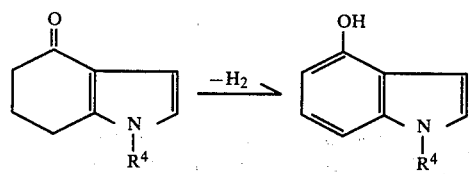

The following examples are further illustrative of this invention and should by no means be construed as being limitative of the invention.

EXAMPLE 1

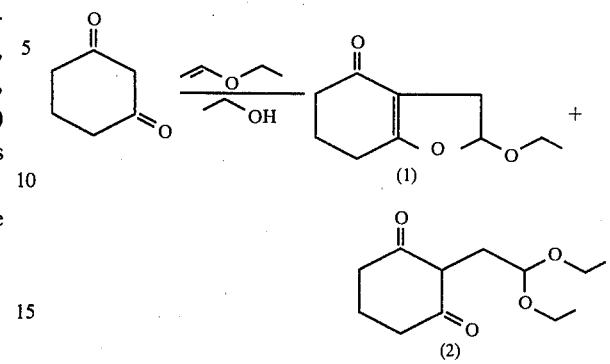

In a 100 ml-beaker, 560 mg of 1,3-cyclohexanedione, 170 mg of sodium ethoxide and 7.5 ml of ethyl vinyl ether were dissolved in 40 ml of distilled ethanol. The beaker was fitted with platinum electrodes (4×3 cm$^2$) and under stirring, electrolysis was carried out at a constant current of 150 mA (current density 12.5 mA/cm$^2$) for 80 minutes (1.5 faradays/mol). After the reaction was completed, the ethanol was distilled off under reduced pressure, a saturated aqueous solution of sodium chloride (about 5 ml) was added to the residue, and the mixture was extracted with ethyl acetate. The extract was washed with a saturated aqueous solution of sodium chloride and dried over anhydrous sodium sulfate. The ethyl acetate was then distilled off and the residue was further distilled under reduced pressure to give 536.3 mg of a colorless to pale yellowish liquid (b.p. 130°–140° C./1–2 mm Hg; Büchi's distillation apparatus). The NMR spectrum of this liquid showed that it contained compounds (1) and (2) in a molar (1)/(2) ratio of 51:49, and its purity as a mixture was 97%.

The saturated aqueous sodium chloride solutions used in the above extraction and washing procedures were acidified with 5% HCl and extracted with ethyl acetate and the extract was dried over anhydrous sodium sulfate. The ethyl acetate was distilled off under reduced pressure to recover 120.8 mg of unreacted 1,3-cyclohexanedione. Thus, the percent conversion, selectivity and yield based on 1,3-cyclohexanedione were 78.5%, 79.3% and 62.3%, respectively.

The structures of these compounds (1) and (2) could be identified from the NMR and MS data on the respective fractions obtained by gas chromatography (silicone DC QF-1, 1 m, column temperature 140° C.).

Compound (1): 2-Ethoxy-4-oxo-2,3,4,5,6,7-hexahydrocoumarone $^1$H-NMR (CDCl$_3$): δ 1.26 (t, J=7.1 Hz, 3H, CH$_3$), 1.90–2.18 (m, 2H, CH$_2$), 2.20–2.60 (m, 4H, CH$_2$C=), 2.64–3.10 (m, 2H, CH$_2$CO), 3.47–4.14 (m, 2H, CH$_2$O), 5.74 (dd, J$_1$=7.1 Hz, J$_2$=3.7 Hz, 1H, CH)

MS (m/e): 182(M$^+$), 153, 137, 126, 98

Compound (2): 2-(2′,2′-Diethoxyethyl)-1,3-cyclohexanedione $^1$H-NMR (CDCl$_3$): δ 1.10–1.30 (m, 6H, CH$_3$), 1.76–2.46 (m, 6H), 2.72–2.96 (m, 2H), 3.34–3.88 (m, 4H, CH$_2$O), 5.08 (dd, J$_1$=5.6 Hz, J$_2$=5.2 Hz, 1H, CH) MS (m/e): 228(M$^+$), 200, 183, 182, 98

EXAMPLE 2

The reaction procedure of Example 1 was repeated except that a current density of 13.9 mA/cm$^2$ was employed and the product was treated and recovered in the same manner. The percent conversion, selectivity and yield were 78.8%, 83.0% and 65.4%, respectively.

EXAMPLE 3

A branched test tube was charged with 112 mg (1 mM) of 1,3-cyclohexanedione, 1.5 ml of ethyl vinyl ether, 0.07 ml of triethylamine and, as solvent, 7 ml of acetonitrile, and using platinum plate electrodes (3 cm²), the mixture was subjected to electrolysis at a constant current of 50 mA and at room temperature. The quantity of electricity was 1.5 F/mol. After the reaction was completed, the acetonitrile was distilled off under reduced pressure, then 4N-aqueous NaOH solution (about 2 ml) was added to the residue, and the mixture was extracted with ethyl acetate. The extract was washed with water and dried over magnesium sulfate, and the ethyl acetate was removed to give 54 mg of a pale yellowish liquid. This liquid gave a substantially single spot on TLC (ether 100%, UV detection) and was confirmed by NMR to be 2-ethoxy-4-oxo-2,3,4,5,6,7-hexahydrocoumarone.

EXAMPLE 4 TO 7

The electrochemical reaction of Example 3 was repeated except that the solvents, basic compounds and auxiliary electrolytes mentioned in Table 1 were used in indicated amounts. Thereby was invariably obtained 2-ethoxy-4-oxo-2,3,4,5,6,7-hexahydrocoumarone as the product. The results are shown in Table 1.

TABLE 1

| Example No. | Solvent (ml) | Basic compound (ml) | Auxiliary electrolyte (mg) | Yield of product (mg) |
|---|---|---|---|---|
| 4 | DMF (6) | Triethylamine (0.07) | — | 54 |
| 5 | DMF (6) | Pyridine (0.2) | Et₄NClO₄ (60) | 18 |
| 6 | DMF (1) Et₂CO₃ (6) | Triethylamine (0.07) | Et₄NClO₄ (120) | 13 |
| 7 | DMSO (10) | Triethylamine (0.04) | — | 31 |

Et = C₂H₅—
DMF = dimethylformamide
DMSO = dimethyl sulfoxide

EXAMPLE 8

A branched test tube of 20 ml capacity was charged with 112 mg of 1,3-cyclohexanedione, 34 mg of sodium ethoxide and 144 mg of n-butyl vinyl ether, followed by addition of 7 ml of ethanol. The test tube was fitted with platinum plate electrodes (2×1.5 cm²) and the above solution was electrolyzed under gentle stirring at a constant current of 50 mA for 96 minutes (3 F/mol). After the reaction was completed, the ethanol was distilled off under reduced pressure and about 1 ml of a saturated aqueous solution of sodium chloride was added to the residue. The organic layer was extracted with ethyl acetate and the extract was washed with aqueous sodium chloride and dried over anhydrous sodium sulfate. The ethyl acetate was then distilled off and the residue was further distilled under reduced pressure to give 110.5 mg of a pale yellowish liquid (b.p. 140°–145° C./1–2 mmHg; Büchi's distillation apparatus). NMR spectrum of this liquid showed that it was a 3:1 (by mol) mixture (purity 95%) of 2-n-butoxy-4-oxo-2,3,4,5,6,7-hexahydrocoumarone

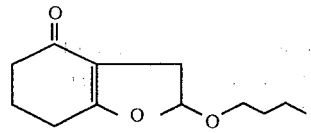

and 2-(2'-ethoxy-2'-n-butoxyethyl)-1,3-cyclohexanedione

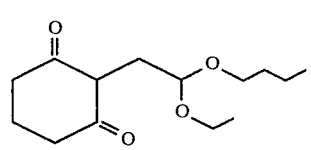

EXAMPLE 9

The reaction procedure of Example 8 was repeated except that 200 mg of isobutyl vinyl ether was used in lieu of n-butyl vinyl ether and the electrolysis was conducted at 1.5 F/mol. The procedure yielded 126.1 mg of a pale yellowish liquid, b.p. 160°–173° C./2 mmHg (Büchi's distillation apparatus). The NMR spectrum of this liquid showed that it was a 2:1 (by mol) mixture (purity 97%) of 2-isobutoxy-4-oxo-2,3,4,5,6,7-hexahydrocoumarone

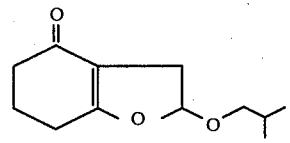

and 2-(2'-ethoxy-2'-isobutoxyethyl)-1,3-cyclohexanedione

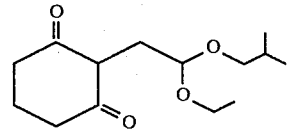

EXAMPLE 10

The reaction procedure of Example 8 was repeated except that 250 mg of cyclohexyl vinyl ether was used in lieu of 144 mg of n-butyl vinyl ether and that 28 mg of KOH was used in lieu of 34 mg of sodium ethoxide, whereby 87 mg of a pale yellow liquid was obtained. NMR of this liquid showed that it was a mixture (mol. ratio=c.a. 1:1; purity 80%) of 2-cyclohexyloxy-4-oxo-2,3,4,5,6,7-hexahydrocoumarone,

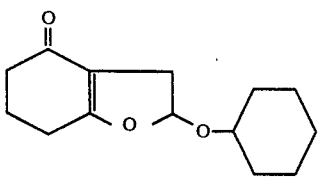

and 2-(2'-ethoxy-2'-cyclohexyloxyethyl)-1,3-cyclohexanedione

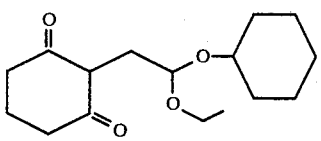

EXAMPLE 11

The reaction product of Example 1 was admixed with the reaction product of Example 3 [the mol. ratio of Compound (1): Compound (2)=87.6:12.4], and 120 mg of this mixture, 68.4 mg of ammonium carbonate and 1 ml of methanol were admixed in a glass tube. The tube was sealed and heated at 150° C. for 14 hours. Then, the methanol was distilled off under reduced pressure, 1 ml of a saturated aqueous solution of sodium chloride was added to the residue and the organic layer was extracted 3 times with 10 ml of ethyl acetate. The ethyl acetate layers were combined, washed with a saturated aqueous solution of sodium chloride and dried over anhydrous sodium sulfate. Removal of the solvent by distillation left 69.5 mg of 4-oxo-4,5,6,7-tetrahydroindole as pale yellow-brown crystals (yield 80.5%). The physico-chemical properties of the product are given below.

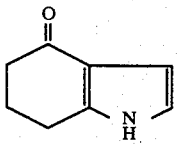

m.p. 183°–184° C.

IR (Nujol): 3460 (NH), 2940, 1640 (C=O), 1470 cm$^{-1}$ $^1$H-NMR (CDCl$_3$): δ 1.98–2.30 (m, 2H, CH$_2$), 2.52 (t, J=6.0 Hz, 2H, CH$_2$), 2.83 (t, J=6.0 Hz, 2H, CH$_2$CO), 6.44–6.72 (m, 2H, CH=), 8.40–9.20 (m, 1H, NH)

EXAMPLE 12

The reactions of Examples 1 and 3 were respectively repeated and the reaction products were admixed in a molar (1)/(2) ratio of 87.6:12.4. Then, 1014 mg of this mixture of 2-ethoxy-4-oxo-2,3,4,5,6,7-hexahydrocoumarone and 2-(2',2'-diethoxyethyl)-1,3-cyclohexanedione, 1.7 ml of liquid ammonia and 5.5 ml of methanol were admixed in a glass tube which was sealed and heated at 100° C. for 1 hour and, then, at 150° C. for 16 hours. The above procedure provided 357.6 mg of 4-oxo-4,5,6,7-tetrahydroindole (yield 49%).

EXAMPLE 13

96.5 mg of 2-ethoxy-4-oxo-2,3,4,5,6,7-hexahydrocoumarone and 1.5 ml of 28% aqueous ammonia were admixed in a glass tube which was sealed and heated at 100° C. for 14 hours. The reaction mixture was treated in the same manner as Example 11 to give 38.4 mg of 4-oxo-4,5,6,7-tetrahydroindole (yield 54%).

EXAMPLE 14

A mixture of 182 mg of 2-ethoxy-4-oxo-2,3,4,5,6,7-hexahydrocoumarone and 1 ml of benzylamine was heated in a glass tube at 110° C. for 12 hours. The reaction mixture was purified by column chromatography on silica gel using a solvent mixture of ethyl acetate and n-hexane (1:1) to give 126 mg of N-benzyl-4-oxo-4,5,6,7-tetrahydroindole as white crystals (yield 56%).

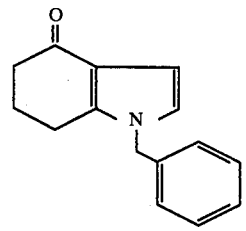

IR (neat): 2940, 1650 (C=O), 1505, 1470 cm$^{-1}$
$^1$H-NMR (CDCl$_3$): δ 1.94–2.24 (m, 2H, CH$_2$), 2.32–2.51 (m, 2H, CH$_2$), 2.64 (t, J=6.1 Hz, 2H, CH$_2$), 5.03 (s, 2H, CH$_2$N), 6.58 (m, 2H, CH=), 6.90–7.40 (m, 5H, Ar)

EXAMPLE 15

The reaction procedure of Example 14 was repeated except that 1 ml of n-butylamine was used in lieu of 1 ml of benzylamine to give 118.4 mg of N-butyl-4-oxo-4,5,6,7-tetrahydroindole (yield 62%).

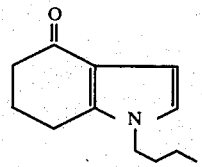

IR (neat): 2940, 2875, 1650(C=O), 1505, 1465 cm$^{-1}$
$^1$H-NMR (CDCl$_3$): δ 0.96 (t, J=6.6 Hz, 3H, CH$_3$), 1.08–1.88 (m, 4H, CH$_2$), 1.98–2.28 (m, 2H, CH$_2$), 2.34–2.56 (m, 2H, CH$_2$), 2.74 (t, J=6.0 Hz, 2H, CH$_2$CO), 3.82 (t, J=7.0 Hz, 2H, CH$_2$N), 6.54 (m, 2H, CH=)

EXAMPLE 16

The reaction procedure of Example 14 was repeated except that 1 ml of n-propylamine was used in lieu of 1 ml of benzylamine to give 106.2 mg of N-propyl-4-oxo-4,5,6,7-tetrahydroindole (yield 60%).

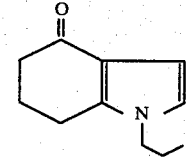

IR (neat): 2950, 2890, 1655 (C=O), 1505, 1465 cm$^{-1}$
$^1$H-NMR (CDCl$_3$): δ 0.94 (t, J=7.0 Hz, 3H, CH$_3$), 1.56–2.00 (m, 2H, CH$_2$), 2.00–2.30 (m, 2H, CH$_2$), 2.40–2.60 (m, 2H, CH$_2$), 2.74 (t, J=6.0 Hz, 2H, CH$_2$O), 3.78 (t, J=7.5 Hz, 2H, CH$_2$N), 6.56 (s, 2H, CH=)

EXAMPLE 17

The reaction procedure of Example 14 was repeated except that 1 ml of cyclohexylamine was used in lieu of 1 ml of benzylamine to give 41.2 mg of N-cyclohexyl-4-oxo-4,5,6,7-tetrahydroindole.

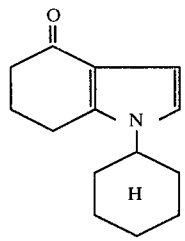

IR (neat): 2940, 2860, 1655 (C=O), 1460 cm$^{-1}$
$^1$H-NMR (CDCl$_3$): δ 1.02–2.6 (m, 14H, CH$_2$, CH), 2.74 (t, J=6.0 Hz, 2H, CH$_2$CO), 3.3–4.2 (m, 1H, CHN), 6.50 (d, J=4.0 Hz, 1H, CH=), 6.64 (d, J=4.0 Hz, 1H, CH=)

EXAMPLE 18

The reaction procedure of Example 14 was repeated except that 1 ml of allylamine was used in lieu of 1 ml of benzylamine to give 70 mg of N-allyl-4-oxo-4,5,6,7-tetrahydroindole.

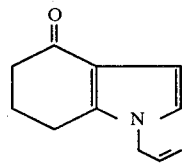

IR (neat): 2950, 2880, 1655 (C=O), 1505, 1470 cm$^{-1}$
$^1$H-NMR (CDCl$_3$): δ1.9–2.6 (m, 4H, CH$_2$), 2.70 (t, J=6 Hz, 2H, CH$_2$), 4.35–4.56 (m, 2H, CH$_2$N), 4.8–5.4 (m, 2H, CH$_2$=), 5.6–6.3 (m, 1H, CH=), 6.55 (s, 2H, CH=)

EXAMPLE 19

A branched test tube of 20 ml capacity was charged with 112 mg of 1,3-cyclohexanedione, 34 mg of sodium ethoxide and 144 mg of n-butyl vinyl ether, followed by addition of 7 ml of ethanol. With platinum electrodes (2×1.5 cm$^2$) fitted to the test tube and the solution kept gently stirred, an electrolysis was carried out at a constant current of 50 mA for 96 minutes (3 F/mol). After the reaction, the ethanol was distilled off under reduced pressure, about 1 ml of a saturated aqueous solution of sodium chloride was added to the residue and the organic layer was taken and extracted with ethyl acetate. The extract was washed with an aqueous solution of sodium chloride and dried over anhydrous sodium sulfate. The ethyl acetate was distilled off and the residue was further distilled under reduced pressure to give 110.5 mg of a pale yellow liquid (b.p. 140°–145° C./1–2 mmHg; Büchi distillation apparatus). NMR of this product showed that it was a mixture (mol. ratio=c.a. 3:1, purity 95%) of 2-n-butoxy-4-oxo-2,3,4,5,6,7-hexahydrocoumarone.

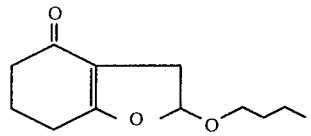

and 2-(2′-ethoxy-2′-n-butoxyethyl)-1,3-cyclohexanedione.

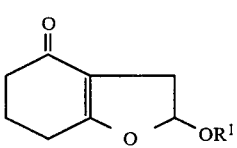

A mixture of 101.3 mg of the above mixture and 1 ml of 28% aqueous ammonia was heated in a glass tube at 100° C. for 16 hours and the reaction mixture was further treated in the same manner as Example 11. By the above procedure was obtained 21.7 mg of 4-oxo-4,5,6,7-tetrahydroindole.

What is claimed is:

1. A cyclohexanone derivative selected from the group consisting of compounds having the formula:

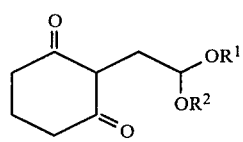

(I)

wherein R$^1$ is a hydrocarbon group of 1 to 15 carbon atoms and compounds having the formula:

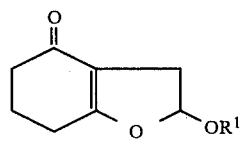

(II)

wherein R$^1$ is as defined above; R$^2$ is a hydrocarbon group of 1 to 15 carbon atoms.

2. A cyclohexanone derivative according to claim 1 which is a derivative having the formula:

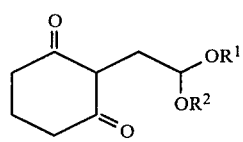

(I)

wherein R$^1$ is an alkyl group of 1 to 15 carbon atoms, a cycloalkyl group of 3 to 15 carbon atoms, an aryl group of 6 to 15 carbon atoms or an aralkyl group of 7 to 15 carbon atoms.

3. A cyclohexanone derivative according to claim 2 which is a 2-lower alkoxy-4-oxo-2,3,4,5,6,7-hexahydrocoumarone.

4. A cyclohexanone derivative according to claim 1 which is a compound having the formula:

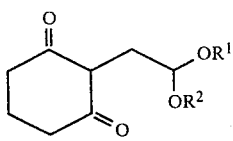 (II)

wherein $R^1$ is an alkyl group of 1 to 15 carbon atoms, a cycloalkyl group of 3 to 15 carbon atoms, an aryl group of 6 to 15 carbon atoms or an aralkyl group of 7 to 15 carbon atoms; $R^2$ is an alkyl group of 1 to 15 carbon atoms, a cycloalkyl group of 5 to 15 carbon atoms or an aralkyl group of 7 to 15 carbon atoms.

5. A cyclohexanone derivative according to claim 4 which is a 2-(2',2'-di-lower alkoxyethyl)-1,3-cyclohexanedione.

* * * * *